(12) United States Patent
Kim et al.

(10) Patent No.: US 9,908,870 B2
(45) Date of Patent: Mar. 6, 2018

(54) CRYSTALLINE FORM OF A BENZIMIDAZOLE DERIVATIVE AND A PREPARATION METHOD THEREOF

(71) Applicant: CJ HEALTHCARE CORPORATION, Seoul (KR)

(72) Inventors: Young Ju Kim, Gyeonggi-do (KR); Eun Sun Kim, Gyeonggi-do (KR); Ji Yun Lee, Gyeonggi-do (KR); Hyuk Woo Lee, Gyeonggi-do (KR); Jae Hong Kweon, Gyeonggi-do (KR); Sung Ah Lee, Gyeonggi-do (KR); Kwang Do Choi, Gyeonggi-do (KR); Dong Hyun Ko, Gyeonggi-do (KR); Seung Pyeong Heo, Seoul (KR)

(73) Assignee: CJ HEALTHCARE CORPORATION, Seoul (KR)

( * ) Notice: Subject to any disclaimer, the term of this patent is extended or adjusted under 35 U.S.C. 154(b) by 0 days.

(21) Appl. No.: 15/543,941

(22) PCT Filed: Nov. 18, 2015

(86) PCT No.: PCT/KR2015/012385
§ 371 (c)(1),
(2) Date: Jul. 14, 2017

(87) PCT Pub. No.: WO2016/117814
PCT Pub. Date: Jul. 28, 2016

(65) Prior Publication Data
US 2018/0009791 A1    Jan. 11, 2018

(30) Foreign Application Priority Data

Jan. 20, 2015 (KR) .................. 10-2015-0009326

(51) Int. Cl.
*C07D 405/12* (2006.01)

(52) U.S. Cl.
CPC ................................ *C07D 405/12* (2013.01)

(58) Field of Classification Search
CPC .................................................... C07D 405/12
See application file for complete search history.

(56) References Cited

U.S. PATENT DOCUMENTS

| 7,723,321 B2 * | 5/2010 | Hanazawa ........... C07D 409/12 514/183 |
|---|---|---|
| 2006/0194969 A1 | 8/2006 | Zimmermann et al. |
| 2008/0214519 A1 | 9/2008 | Koike et al. |

FOREIGN PATENT DOCUMENTS

| KR | 10-2011-0038011 A | 4/2011 |
| KR | 10-1088247 B | 11/2011 |
| KR | 10-2012-0052269 A | 5/2012 |

* cited by examiner

*Primary Examiner* — Shawquia Jackson

(57) ABSTRACT

The present invention relates to a novel crystalline form of a benzimidazole derivative and a preparation method thereof.

The novel crystalline form according to the present invention is hardly changed chemically and/or physically under a long-term photo-stressed condition, has a low hygroscopicity, and has an extremely low static-electricity-inducing capability, thus being advantageous for formulation, and due to the excellent stability of the crystal form itself, it is very useful for long-term storage of the compound.

11 Claims, 3 Drawing Sheets

CRYSTALLINE FORM OF A BENZIMIDAZOLE DERIVATIVE AND A PREPARATION METHOD THEREOF

CROSS-REFERENCES TO RELATED APPLICATIONS

This application is a U.S. national phase application of International PCT Patent Application No. PCT/KR2015/012385, which was filed on Nov. 18, 2015, which claims priority to Korean Patent Application Nos. 10-2015-0009326, filed Jan. 20, 2015. These applications are incorporated herein by reference in their entireties.

TECHNICAL FIELD

The present invention relates to a novel crystalline form of a benzimidazole derivative defined by a particular X-ray powder diffraction pattern, and a preparation method thereof.

BACKGROUND ART

Generally, when a drug is present in various forms including a non-crystalline form, one or more kinds of crystalline form etc., it is obvious in the art that pharmaceutically important factors such as solubility, release characteristics, and bioavailability may vary among their forms. Particularly, in a compound where optical isomers can be present, each isomer may exhibit differences not only in physico-chemical properties but also in pharmacological activities and toxicities. Therefore, it is very important to manufacture and/or separate an optical isomer having high pharmacological activity and low toxicity with high-purity. Specifically, regarding polymorphic crystalline forms, if multiple types of crystalline forms are mixed upon completion of the entire formulation procedure due to the occurrence of changes in polymorphic crystalline forms, it may lead to a change in the pharmaceutical properties of the final drug and thereby induce unexpected pharmacokinetic responses. Accordingly, it is very important to obtain a compound in a pure, single crystalline form in order to secure reproducibility of the drug.

Furthermore, in selecting from various crystalline forms, or between a crystalline form and a non-crystalline form, the non-crystalline form has advantages of increasing pharmaceutical efficacy and exhibiting fast action due to its high solubility in general. However, the non-crystalline form has disadvantages of a short shelf-life and difficulty in adjusting the release speed and blood concentration of the drug due to instability. In contrast, the crystalline form, although it has low solubility and thus has a low bioavailability per unit weight, also has advantages in that it can secure stability and prepare formulations capable of long-acting release. As such, because the crystalline form has higher stability and lower solubility than the non-crystalline form, it is necessary to sacrifice solubility when stability is given top priority, whereas stability may be sacrificed when solubility should be considered first, thus making the decision on how to meet both stability and solubility is difficult.

DISCLOSURE

Technical Problem

The present inventors have made many efforts to develop a form of compound having long-term storage stability and industrial applicability in order to utilize 4-[((4S)-5,7-difluoro-3,4-dihydro-2H-chromen-4-yl)oxy]-N,N,2-trimethyl-1H-benzimidazole-6-carboxamide ("Formula 1 compound", hereinafter), which is one of the benzimidazole derivatives known to have an acid pump inhibition activity, for formulation purposes. As a result, they discovered that the novel crystalline form of the compound having a particular X-ray powder diffraction pattern is hardly changed chemically and/or physically under a long-term photo-stressed condition, has a low hygroscopicity, and has an extremely low static-electricity-inducing capability, and is thus advantageous for formulation, and due to the excellent stability of the crystal form itself, it is very useful for long-term storage of the compound, thereby completing the present invention.

[Formula 1]

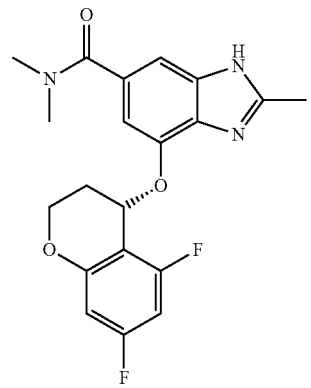

Technical Solution

An object of the present invention is to provide a novel crystalline form of a compound of Formula 1, which is easy to prepare and has excellent stability.

Advantageous Effects

The crystalline form A of a compound represented by the following Formula 1 according to the present invention, compared to the non-crystalline compound, is hardly changed chemically and/or physically under a long-term photo-stressed condition, has a low hygroscopicity, and has an extremely low static-electricity-inducing capability, thus being advantageous for formulation, and due to the excellent stability of the crystal form itself, it is very useful for long-term storage of the compound.

BEST MODE

Figure 1:
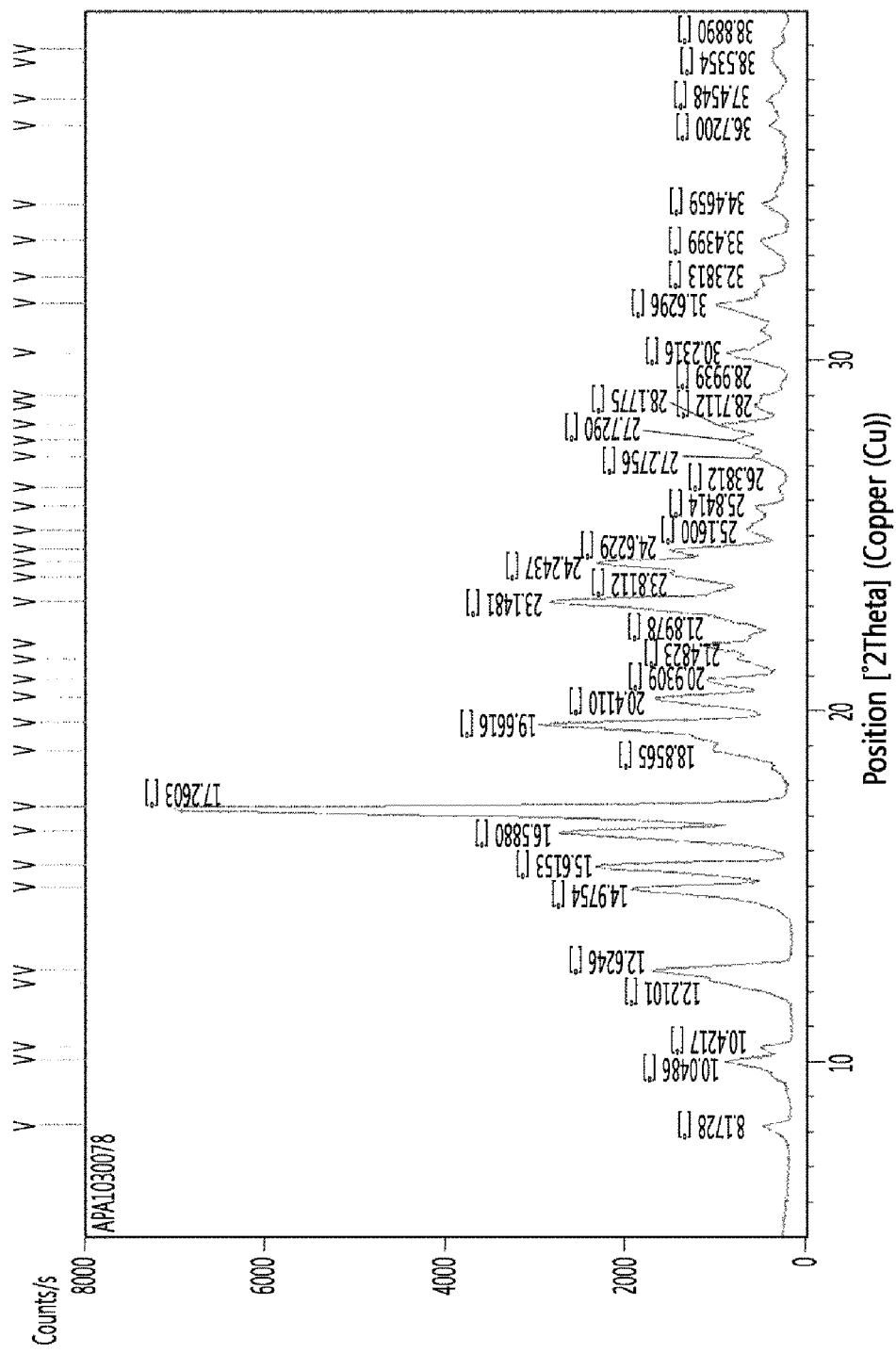
FIG. 1 presents an X-ray diffractogram of a novel crystalline form A of the Formula 1 compound according to an exemplary embodiment of the present invention.

In order to accomplish the above objects, the present invention provides a crystalline form A of compound represented by the following Formula 1 having an X-ray powder diffraction pattern with peaks at diffraction angles of 8.1°, 10.0°, 12.6°, 14.9°, 15.6°, 16.5°, 17.2°, 19.6°, 23.1°, 24.2°, 28.1°, 30.2°, and 31.6° (2θ±0.2°).

[Formula 1]

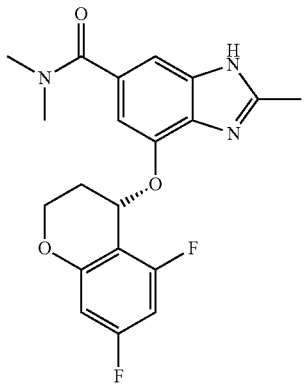

The novel crystalline form provided in the present invention may be further specified as described herein below.

For example, the crystalline form A of the compound represented by Formula 1 is characterized in that it has an endothermal peak at a temperature between 220° C. and 225° C. in differential scanning calorimetry.

Additionally, the crystalline form A of the compound represented by Formula 1 is characterized in that it has an IR spectrum with characteristic absorption peaks at 832 cm$^{-1}$, 1071 cm$^{-1}$, 1127 cm$^{-1}$, 1326 cm$^{-1}$, 1403 cm$^{-1}$, 1440 cm$^{-1}$, 1598 cm$^{-1}$, 2934 cm$^{-1}$, 3062 cm$^{-1}$, and 3124 cm$^{-1}$.

In another aspect, the present invention provides a method of preparing a crystalline form A of a compound represented by Formula 1 comprising suspending the compound represented by Formula 1 in any random form in acetonitrile or water; subjecting the resulting solution to heat-treatment while stirring for 1 hour to 24 hours; and cooling the resulting solution to room temperature followed by ripening crystals while stirring for 1 hour to 48 hours.

In particular, the stirring with heat-treatment may be performed by increasing the temperature up to from 50° C. to 120° C.

In still another aspect, the present invention provides a method of preparing a crystalline form A of a compound represented by Formula 1 comprising dissolving the compound represented by Formula 1 in any random form in $C_{1-4}$ alcohol or acetone; crystallizing the compound by adding an antisolvent to the resulting solution; and ripening the resulting crystal while stirring for 6 hours to 24 hours at room temperature.

In particular, the $C_{1-4}$ alcohol may be methanol, and the antisolvent may be water or isopropyl ether, but are not limited thereto.

As used herein, the term "antisolvent" refers to a solvent which shows low solubility or insolubility to a target compound, and can be used to precipitate a target compound by adding it to a solution in which the target compound is dissolved. Therefore, in the method of preparing the crystalline form A according to the present invention, the crystallization of a compound can be achieved by adding an appropriate antisolvent to the solution where the compound is already dissolved, considering the solvent type and the solubility of the compound in the solvent, etc. The crystals produced therein may have an X-ray powder diffraction pattern, an endothermal peak, and/or an IR spectrum with characteristic absorption peaks as described above.

Additionally, in order to obtain the product with high purity by removing impurities, remaining solvents, etc., the method may further comprise filtering or drying. The filtering and/or drying may be performed without limitation using a method known in the art.

MODE FOR INVENTION

Hereinafter, the present invention will be described in more detail with reference to the following Examples. However, these Examples are for illustrative purposes only, and the invention should not be limited by these Examples.

Example 1: Preparation of Crystalline Form A Using Acetonitrile 50 g of (−)-4-[((4S)-5,7-difluoro-3,4-dihydro-2H-chromen-4-yl]oxyl-N,N,2-trimethyl-1H-benzimidazole-6-carboxamide was added to 400 mL of acetonitrile, and the mixed solution was heated until its inner temperature reached 60° C. The mixed solution was stirred for 3 hours at the same temperature, and then slowly cooled to room temperature. The crystals were ripened by stirring the mixed solution for an additional 3 hours and the resulting solid was filtered. The harvested solid was dried at 40° C. under vacuum to obtain 45 g of the title compound, the crystalline form A of the Formula 1 compound (yield: 90%, m.p.: 222±3° C.).

Example 2: Preparation of Crystalline Form A Using Methanol 50 g of (−)-4-[((4S)-5,7-difluoro-3,4-dihydro-2H-chromen-4-yl]oxyl-N,N,2-trimethyl-1H-benzimidazole-6-carboxamide was added to 100 mL of methanol and dissolved. The compound was crystallized by adding the mixed solution to 900 mL of distilled water dropwise. The crystals were ripened by stirring the mixed solution at room temperature for 12 hours, and the resulting solid was filtered. The harvested solid was dried at 40° C. under vacuum to obtain 46 g of the title compound, the crystalline form A of Formula 1 compound (yield: 92%, m.p.: 222±3° C.).

Example 3: Preparation of Crystalline Form A Using Purified Water 50 g of (−)-4-[((4S)-5,7-difluoro-3,4-dihydro-2H-chromen-4-yl]oxyl-N,N,2-trimethyl-1H-benzimidazole-6-carboxamide was added to 250 mL of purified water, and the mixed solution was heated until its inner temperature reached 100° C. The mixed solution was stirred for 12 hours at the same temperature, and then slowly cooled to room temperature. The crystals were ripened by stirring the mixed solution for an additional 36 hours and the resulting solid was filtered. The harvested solid was dried at 40° C. under vacuum to obtain 49 g of the title compound, the crystalline form A of the Formula 1 compound (yield: 98%, m.p.: 222±3° C.).

Example 4: Preparation of a Crystalline Form A Using Acetone 50 g of (−)-4-[((4S)-5,7-difluoro-3,4-dihydro-2H-chromen-4-yl]oxyl-N,N,2-trimethyl-1H-benzimidazole-6-carboxamide was added to 250 mL of acetone and dissolved.

The compound was crystallized by adding the mixed solution to 500 mL of isopropyl ether dropwise. The crystals were ripened by stirring the mixed solution for an additional 12 hours and the resulting solid was filtered. The harvested solid was dried at 40° C. under vacuum to obtain 45 g of the title compound, the crystalline form A of the Formula 1 compound (yield: 90%, m.p.: 222±3° C.).

Comparative Example 1: Preparation of a Non-Crystalline Compound

The non-crystalline compound 1 was prepared according to the method disclosed in Example 2 of Japanese Patent No. 4481344.

Experimental Example 1: X-Ray Diffraction Spectroscopy Analysis of Crystalline Form A For the X-ray powder diffraction analysis of the crystalline form A of 4-[((4S)-5,7-difluoro-3,4-dihydro-2H-chromen-4-yl)oxy]-N,N,2-trimethyl-1H-benzimidazole-6-carboxamide prepared in Examples 1 to 4, spectra were measured and analyzed using a STOE grazing incidence diffraction measurement device (X-ray wavelength: 0.01 Å to 100 Å, scanning speed/second: 0.02), and the representative result is shown in FIG. 1.

Specifically, the crystalline form A of 4-[((4S)-5,7-difluoro-3,4-dihydro-2H-chromen-4-yl]oxyl-N,N,2-trimethyl-1H-benzimidazole-6-carboxamide of the present invention prepared in Examples 1 to 4 were all confirmed in the X-ray diffractogram to have characteristic peaks at diffraction angles of 8.1°, 10.0°, 12.6°, 14.9°, 15.6°, 16.5°, 17.2°, 19.6°, 23.1°, 24.2°, 28.1°, 30.2°, and 31.6° (2θ±0.2°) (FIG. 1).

Experimental Example 2: IR Spectrum Analysis of Crystalline Form A

Figure 2:
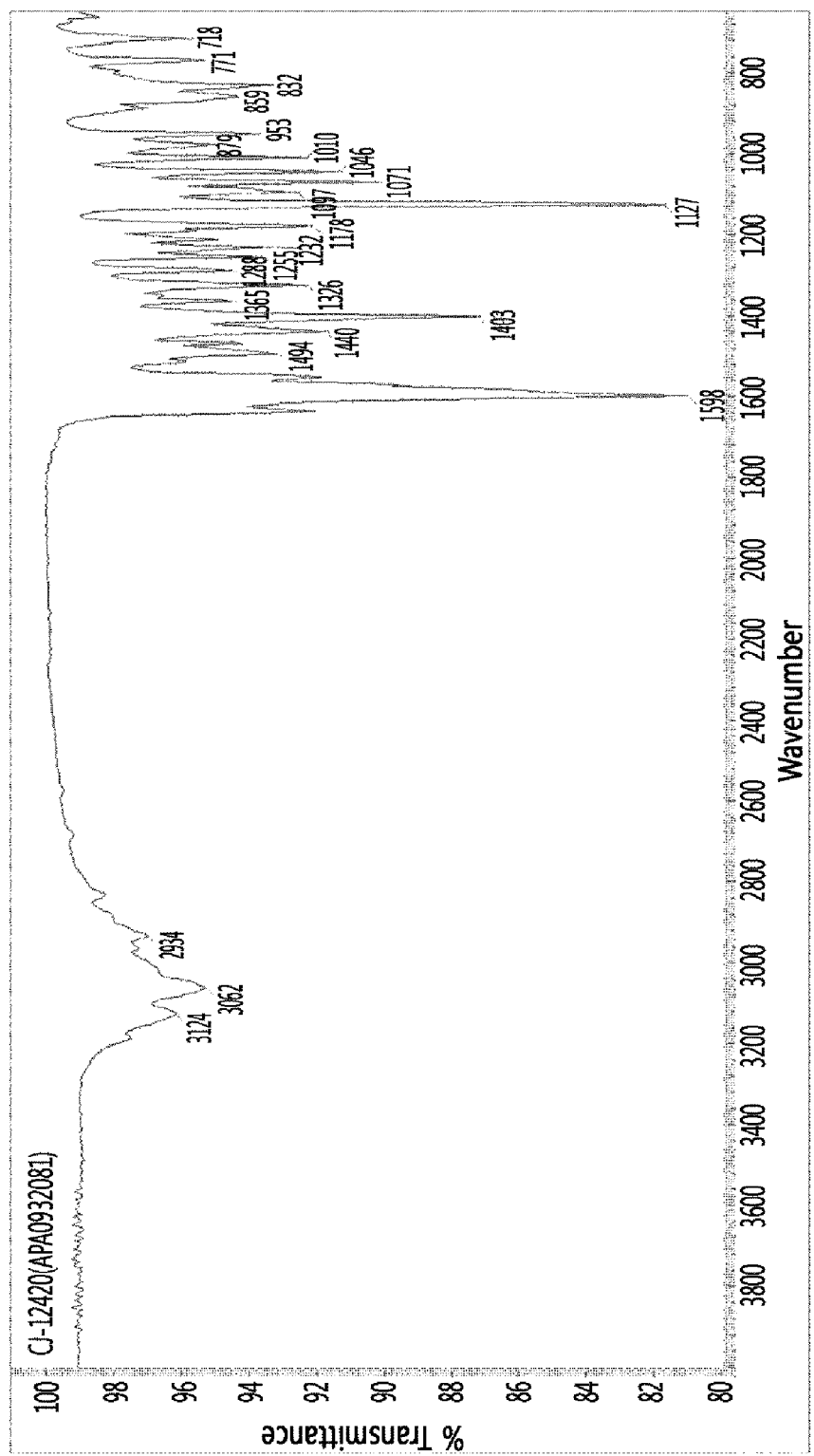
FIG. 2 presents an IR spectrum of a novel crystalline form A of the Formula 1 compound according to an exemplary embodiment of the present invention.

IR spectrum analyses were performed for the crystalline form A of the Formula 1 compounds prepared in Examples 1 to 4. The spectrum measurements and analyses were performed using Fourier-IR Spectrometer (Bruker Corporation) and the representative result is shown in FIG. 2. From the FIG. 2, it was confirmed that all crystalline form A of the Formula 1 compounds prepared in Examples 1 to 4 of the present invention had IR spectra with characteristic absorption peaks at 832 $cm^{-1}$, 1071 $cm^{-1}$, 1127 $cm^{-1}$, 1326 $cm^{-1}$, 1403 $cm^{-1}$, 1440 $cm^{-1}$, 1598 $cm^{-1}$, 2934 $cm^{-1}$, 3062 $cm^{-1}$, and 3124 $cm^{-1}$.

Figure 3:
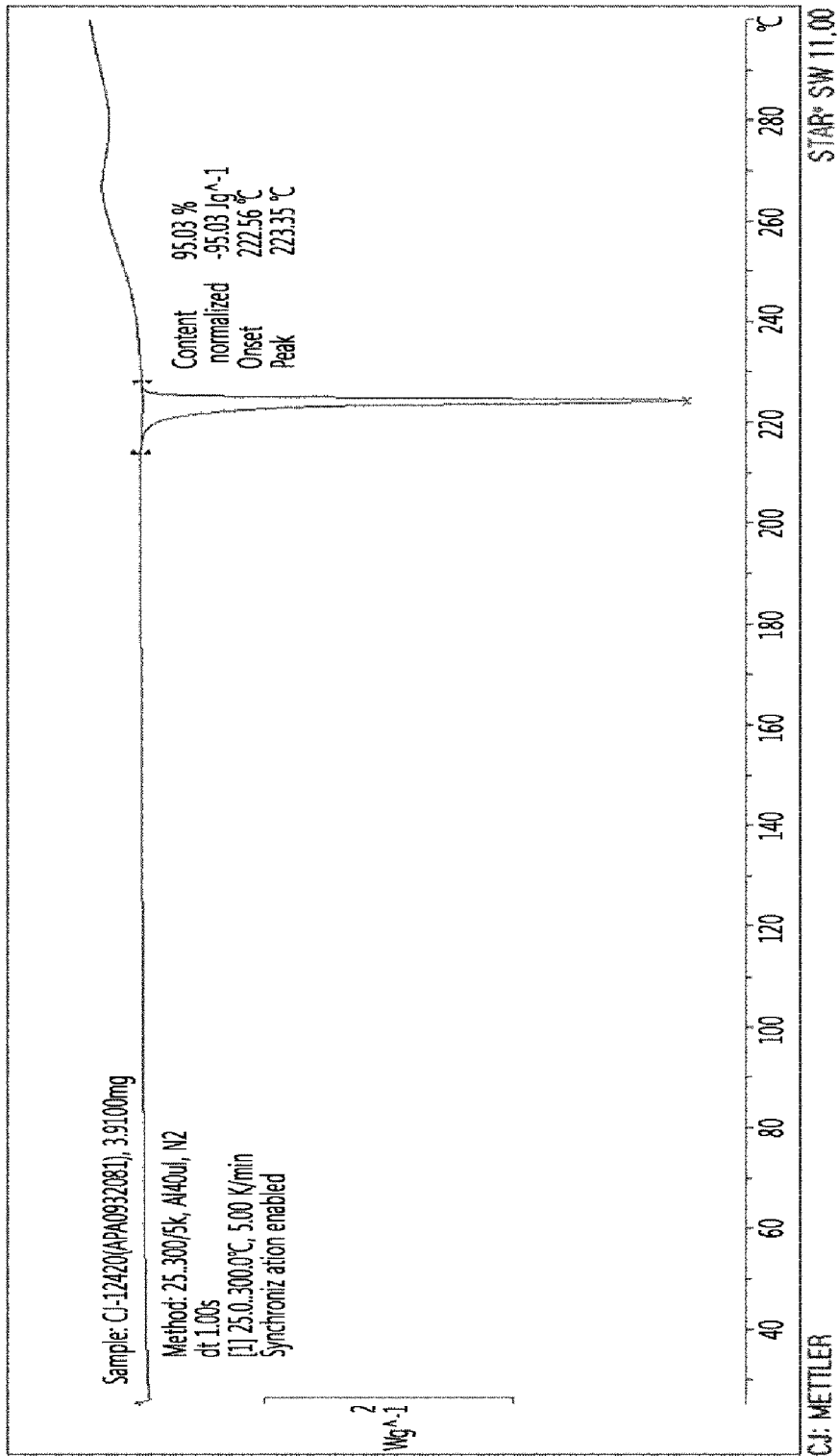
FIG. 3 presents a thermogram of a novel crystalline form A of the Formula 1 compound according to an exemplary embodiment of the present invention by DSC (differential scanning calorimetry).

Experimental Example 3: Differential Scanning Calorimetry Analysis of Crystalline Form A Differential scanning calorimetry (DSC) was performed for the crystalline form A of the Formula 1 compounds prepared in Examples 1 to 4. The DSC thermal analyzer from TA Instruments was used to analyze the DSC thermogram and the representative result is shown in FIG. 3. From the results, it was confirmed that all crystalline form A of the Formula 1 compounds prepared in Examples 1 to 4 of the present invention had endothermal peaks at a temperature between 220° C. and 225° C.

From the Experimental Examples above, it was confirmed that all crystalline form A of the Formula 1 compounds prepared in Examples 1 to 4 had the same characteristics. Accordingly, further experiments were performed using the representative crystalline form A of the Formula 1 compound prepared in Example 1.

Experimental Example 4: Stability Test of Crystalline Form A Under a Photo-Stressed Condition In order to examine the stability of the crystalline form A of the Formula 1 compound prepared in Example 1 under a photo-stressed condition, the compound was exposed at given test conditions, i.e., 1,200,000 lux or higher and 200 $W/m^2$ or higher, and the changes in its appearance, optical purity, and content of related compounds were measured. Additionally, the change in color was observed by the naked eye, and the results are shown in Table 1 below.

TABLE 1

| Crystal form | Non-crystalline form | | Crystalline form A | |
|---|---|---|---|---|
| Period | initial stage | after 4 weeks | initial stage | after 4 weeks |
| Appearance | white powder | yellow powder | white powder | white powder |
| Content of optical isomers | 0.04% | 0.47% | N.D. | N.D. |
| Content of impurities | 0.16% | 0.49% | 0.10 | 0.10 |

As shown in Table 1, the crystalline form A of the Formula 1 compound was shown to have excellent optical purity compared to the non-crystalline form. Additionally, no optical isomer was detected in the crystalline form A, i.e., 100% optical purity was maintained, even after exposed under a photo-stressed condition for 4 weeks, whereas the content of optical isomers was increased by 10-fold in the non-crystalline form thereby markedly decreasing its optical purity. Additionally, when observed with the naked eye, the non-crystalline form showed a white color as the pure compound, and gradually turned yellow due to exposure to light, whereas no noticeable color change was observed in the crystalline form A under the same condition. Furthermore, the crystalline form A was shown to maintain a content of related compounds of 0.1% or below, which is a standard value for pharmaceutical drug approval, not only as it was but after treated under a 4-week photo-stressed condition, whereas the non-crystalline form showed related compounds content of 0.16%, which was higher than the previously mentioned standard value, for the compound itself, and its content of related compounds increased by 3-fold or more after a 4-week photoexposure. From these results, it is obvious that there will be marked differences between the two forms in terms of optical purity and the content of related compounds, considering more than one year of shelf-life required for conventional pharmaceutical drugs from manufacture to distribution to customers.

Conclusively, these results demonstrate that the crystalline form A of 4-[((4S)-5,7-difluoro-3,4-dihydro-2H-chromen-4-yl)oxy]-N,N,2-trimethyl-1H-benzimidazole-6-carboxamide according to the present invention has excellent photostability compared to the same compound in a non-crystalline form, prepared in Comparative Example 1.

Experimental Example 5: Hygroscopicity Test of Crystalline Form A

Compounds with low hygroscopicity are advantageous in preparing formulations, and also are advantageous for storage. Additionally, compounds with high hygroscopicity are not advantageous in that they are difficult to formulate, and reproducible results may hardly be obtained even though formulations can be successfully achieved. In this regard, the hygroscopicity of the crystalline form A of 4-[((4S)-5,7-difluoro-3,4-dihydro-2H-chromen-4-yl]oxyl-N,N,2-trimethyl-1H-benzimidazole-6-carboxamide according to the present invention was measured and compared with those of the non-crystalline compounds, and the results are shown in Table 2 below.

TABLE 2

| Crystal form | Non-crystalline form | | Crystalline form A | |
|---|---|---|---|---|
| Period | initial stage | after 4 weeks | initial stage | after 4 weeks |
| 33% RH | 1.32 | 1.90 | N.D. | 0.17 |
| 75% RH | | 4.09 | | 0.20 |
| 93% RH | | 5.25 | | 0.28 |

As shown in Table 2, the non-crystalline compound at the initial stage showed a hygroscopicity of 1.32, and the hygroscopicity measured after 4 weeks increased markedly, along with the increase in relative humidity. In contrast, the crystalline form A compound itself did not show any hygroscopicity, but, after being stored in conditions of 33%, 75%, and 93% relative humidity for 4 weeks, respectively, it showed a gradual increase in hygroscopicity values, although the values were still as low as to be below 0.3, corresponding to 5% to 9% of that of the non-crystalline compound. From these results, it was confirmed that the crystalline form A compound has significantly lower hygroscopicity than that of the same compound in a non-crystalline form, and is thus useful for preparing formulations and storage.

Experimental Example 6: Static-Electricity Inducibility Test of Crystalline Form A Considering that materials with high inducibility of static-electricity are generally difficult to handle under the conditions of the pharmaceutical technology, and in particular under the pharmacological conditions for conventional industrial crude drugs, and are also not easily realized as drugs with uniform content, the static-electricity inducibility of the crystalline form A of the Formula 1 compound of the present invention was examined and compared with those of the same compounds in non-crystalline form, and the results are shown in Table 3 below.

TABLE 3

| API Form | BD (g/mL) | TD (g/mL) | CI* (%) |
|---|---|---|---|
| Non-crystalline form | 0.23 | 0.39 | 41.02 |
| | 0.22 | 0.38 | 42.11 |
| Crystalline form A | 0.34 | 0.45 | 24.44 |
| | 0.32 | 0.45 | 28.89 |

*Carr's Index (CI): ≤30 value - good flowability

As shown in Table 3, the crystalline form A of the Formula 1 compound of the present invention was shown to have higher bulk density (BD) and tapped density (TD), compared to that of the non-crystalline compound, respectively. The CI values obtained from these parameters by the following equation were in the range from 24% to 29%, much lower than the CI values of from 41% to 42% for the non-crystalline compound, thus confirming that the crystalline form A of the Formula 1 compound of the present invention has significantly lower static-electricity inducibility and excellent flowability compared to that of the non-crystalline compound.

$$CI = 100 \times (1 - BD/TD).$$

From the above, it was confirmed that, because the crystalline form A of the Formula 1 compound of the present invention has lowered static-electricity inducibility and improved flowability, unlike the non-crystalline compound which is difficult to formulate due to its low density and high static-electricity, formulations are prepared using the crystalline form A of the Formula 1 compound of the present invention, and it has advantageous physicochemical properties to improve convenience in preparation and to enhance content uniformity during the formulation process.

Experimental Example 7: Crystal Stability of Crystalline Form A

Finally, a crystal stability test was performed to examine the stability of the crystalline form itself, and the results are shown in Table 4 below.

TABLE 4

| API form | Crystalline form | DSC (° C.) |
|---|---|---|
| Initial stage | crystalline form A | 223 |
| After 4 weeks | crystalline form A | 223 |

As shown in Table 4, the crystalline form A of the compound represented by Formula 1 was shown to maintain the crystalline form A as a form of an active pharmaceutical ingredient (API), which is the same as in the initial stage, after the 4-week treatment under severe stability testing conditions (60±2° C., 80±5% RH). This suggests that the crystalline form A of the compound represented by Formula 1 can maintain its physicochemical properties without any change in crystalline characteristics even after long-term storage, thus having an advantage enabling long-term storage.

The invention claimed is:

1. A crystalline form A of a compound represented by the following Formula 1 having an X-ray powder diffraction pattern with peaks at diffraction angles of 8.1°, 10.0°, 12.6°, 14.9°, 15.6°, 16.5°, 17.2°, 19.6°, 23.1°, 24.2°, 28.1°, 30.2°, and 31.6° (2θ±0.2°):

[Formula 1]

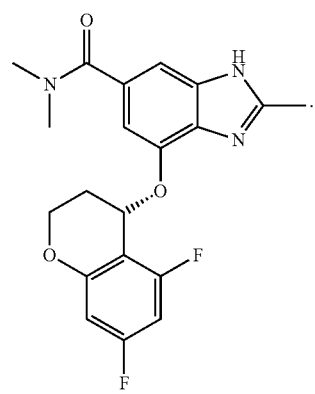

2. The crystalline form A of claim 1, wherein the crystalline form A has an endothermal peak at a temperature between 220° C. and 225° C. in differential scanning calorimetry.

3. The crystalline form A of claim 1, wherein the crystalline form A has an IR spectrum with characteristic absorption peaks at 832 cm$^{-1}$, 1071 cm$^{-1}$, 1127 cm$^{-1}$, 1326 cm$^{-1}$, 1403 cm$^{-1}$, 1440 cm$^{-1}$, 1598 cm$^{-1}$, 2934 cm$^{-1}$, 3062 cm$^{-1}$, and 3124 cm$^{-1}$.

4. A method of preparing a crystalline form A of a compound represented by the following Formula 1, comprising:
   suspending the compound represented by Formula 1 in any random form in a solvent selected from the group consisting of acetonitrile, C$_{1-4}$ alkylacetate, C$_{1-4}$ dichloroalkane, chloroform, tetrahydrofuran, toluene, di(C$_{1-4}$ alkyl)ether, (C$_{1-4}$ alkyl)(C$_{1-4}$ alkyl)ether, C$_{1-4}$ alkyl ether, water and a mixture thereof;
   subjecting the resulting solution to heat-treatment while stirring for 1 hour to 24 hours; and
   cooling the resulting solution to room temperature followed by ripening crystals while stirring for 1 hour to 48 hours:

[Formula 1]

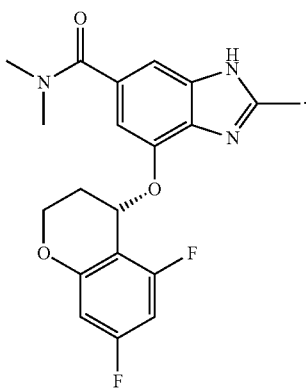

5. The method of claim 4, wherein the solvent is acetonitrile, methyl acetate, ethyl acetate, isopropyl acetate, 1,2-dichloroethane, methylene chloride, chloroform, tetrahydrofuran, toluene, diethyl ether, isopropyl ether, tert-butyl methyl ether, water or a mixture thereof.

6. The method of claim 4, wherein the heat-treatment is to increase the temperature up to from 50° C. to 120° C.

7. A method of preparing a crystalline form A of a compound represented by the following Formula 1, comprising:
   dissolving the compound represented by Formula 1 in any random form in a solvent selected from the group consisting of C$_{1-4}$ alcohol, acetone, and a mixture thereof;
   crystallizing the compound by adding an antisolvent to the resulting solution; and
   ripening the resulting crystal while stirring for 6 hours to 24 hours at room temperature:

[Formula 1]

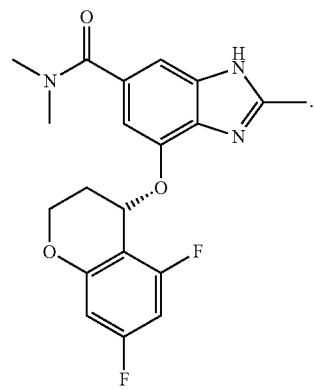

8. The method of claim 7, wherein the solvent is methanol, ethanol, isopropanol, n-propanol, n-butanol, isobutanol, t-butanol, acetone, or a mixture thereof.

9. The method of claim 7, wherein the antisolvent is water, isopropyl ether, acetonitrile, diethyl ether, tert-butyl methyl ether, or a mixture thereof.

10. The method of claim 4, further comprising filtering or drying.

11. The method of claim 7, further comprising filtering or drying.

* * * * *